United States Patent [19]

Nasu et al.

[11] Patent Number: 4,823,082

[45] Date of Patent: Apr. 18, 1989

[54] SIGNAL PROCESSING METHOD FOR AN ELECTROMAGNETIC INDUCTION TEST

[75] Inventors: Shoji Nasu, Kobe; Yoshiro Nishimoto, Higashiosaka; Hiroaki Yasukuni, Kobe; Masayoshi Iwasaki, Miki, all of Japan

[73] Assignee: Kabushiki Kaisha Kobe Seiko Sho, Kobe, Japan

[21] Appl. No.: 13,424

[22] Filed: Feb. 11, 1987

[30] Foreign Application Priority Data

Feb. 18, 1986 [JP] Japan .................. 61-34498
Feb. 18, 1986 [JP] Japan .................. 61-34497
Apr. 10, 1986 [JP] Japan .................. 61-83921

[51] Int. Cl.$^4$ ...................... G01N 27/90; G01R 33/12
[52] U.S. Cl. ..................................... 324/232; 324/225; 324/233; 324/242
[58] Field of Search ............... 324/225, 227, 232, 233, 324/238, 240–243

[56] References Cited

U.S. PATENT DOCUMENTS 3,706,029 12/1972 Wandling .
4,061,968 12/1977 Pigeon .
4,326,166 4/1982 Pigeon et al. .................. 324/233 X
4,628,260 12/1986 Kimoto et al. .................. 324/233 X
4,628,261 12/1986 Huschelrath et al. .......... 324/227 X

FOREIGN PATENT DOCUMENTS 2630290 1/1978 Fed. Rep. of Germany .
2739873 3/1979 Fed. Rep. of Germany .
2913877 10/1979 Fed. Rep. of Germany .
2570500 3/1986 France .
999917 7/1965 United Kingdom .
2019005 10/1979 United Kingdom .

OTHER PUBLICATIONS

Patent Abstracts of Japan, vol. 9, No. 320, (P-413) [2043], Dec. 14, 1985; & JP-A-60 146 149 (SUMITOMO KINZOKU KOGYO K.K.), 01/08/1985.

Primary Examiner—Gerard R. Strecker
Attorney, Agent, or Firm—Oblon, Fisher, Spivak, McClelland & Maier

[57] ABSTRACT

A signal processing method in an electromagnetic induction test. A test object is subjected to an electromagnetic induction by use of N ($N \geq 1$) kinds of test frequencies to obtain M ($M \leq 2N$) kinds of phase detection outputs corresponding to respective states of the test object. The phase detection outputs are then sampled at a plurality of measuring points so that there exists n ($n < M$) kinds of disturbance factors of which a portion contribute to the electromagnetic induction test. The phase detection outputs have a variance greater than a variance of a target parameter of the test object and contribute to the electromagnetic induction test. A first coordinate axis $Z_1$ is determined in a direction in which a variance of a distribution of the group of the measuring points comes to be a maximum in an M-dimensional space formed with the coordinate axes associated with the M kinds of the phase detection outputs. The remaining coordinate axes are likewise determined. Based on the coordinate of each of the measuring points viewed from the coordinate axis $Z_{n+1}$, a measuring is effected to determine a presence or an absence of a defect, a physical quantity, and a geometric quantity on a surface of the test object.

5 Claims, 5 Drawing Sheets

PRESENCE OF DEFECT

MEASUREMENT INTERVAL

FIG. 3(b)

MEASUREMENT INTERVAL

COMPONENT DELAYED BY 90° WITH RESPECT TO OUTPUT FROM A.C. POWER SUPPLY

COMPONENT WITH SAME PHASE AS THAT OF OUTPUT FROM A.C. POWER SUPPLY

SIGNAL PROCESSING METHOD FOR AN ELECTROMAGNETIC INDUCTION TEST

BACKGROUND OF THE INVENTION

1. Field of the Invention

The present invention relates generally to a signal processing method and more particularly to a signal processing method in an electromagnetic test (to be referred to as ECT herebelow). The test measures a defect, a physical quantity, and a geometrical quantity on a surface of a conductive test object or in the proximity of the surface thereof by the use of an induced current (an eddy current) and a defect detector using the electromagnetic induction test.

2. Discussion of Background

The fundamental principle of the ECT is that a coil with an alternating current (with a frequency ranging from 100 Hz to several megaherz) flowing therethrough is placed in the neighborhood of a conductive test object. A current (eddy current) is induced therethrough and the disturbance of the induced current is detected as a change in the impedance of the coil or a change in the induced voltage, thereby detecting a defect, a physical quantity, and a geometric quantity of the test object. Incidentally, in addition to the defect, the physical quantity, and the geometric quantity to be detected, the phase detection output of the ECT also depends on such various factors or parameters at the same time as the lift-off (the distance between the coil and the test surface), the roughness of the test surface, and temperatures of the coil and the test object which effect the induced current. Consequently, for an ECT with a high precision, it is necessary to separate the various noise factors from the factors of the detection object.

Figure 9A:
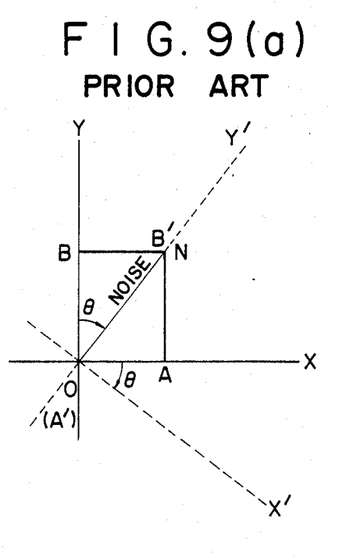
FIGS. 9a, 9b, 10 and 11 are explanatory diagrams for explaining a conventional example.
Figure 9B:
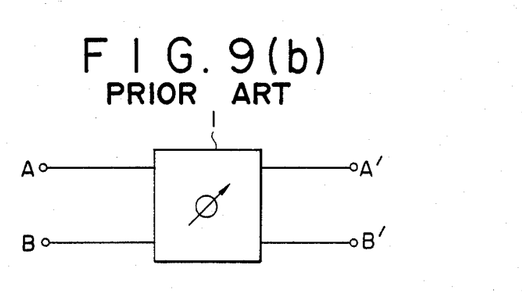

FIGS. 9a-9b are explanatory diagrams illustrating one of the conventional examples of the signal processing method for separating and removing the noise factors in the ECT ("Eddy Current Defect Detecting Test B", NDI, '84, p. 114). This conventional example can be applied to a case where only a single noise factor is present, the alternating current (ac) to be applied to the coil has a single test frequency, and a coordinate rotation is effected as shown in FIG. 9a so that in a plane in which two orthogonal axes are formed with phase detection outputs X and Y obtained from the eddy current defect detector, the indication of the noise factor is parallel to one of these axes. FIG. 9b is a block diagram illustrating an apparatus for effecting the processing of the coordinate rotation in which reference numeral 1 indicates a coordinate rotating unit. With the provision of the coordinate rotation processing, the signals in a direction orthogonal to the axis parallel to the indication of the noise factor become free from the effect of the noise, which makes it possible to detect with a high precision a signal corresponding to the factor or parameter of the detection object to be measured.

However, the indication of the noise factor does not actually lead to a sharp image of indication as shown in FIG. 9a. Namely, there exists a fluctuation of the values in this direction. Consequently, the noise factor cannot be removed to a sufficient degree in the prior art example.

Figure 10:
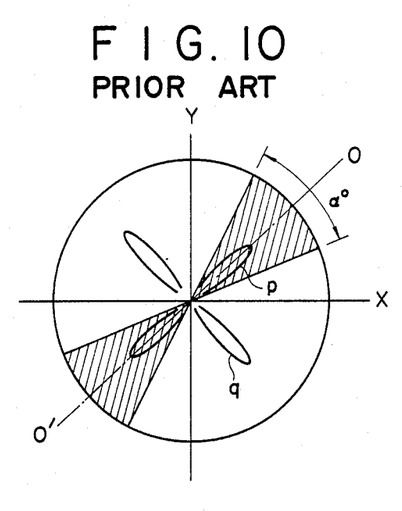

To overcome this difficulty, there has been disclosed a method (the Japanese patent laid-open No. 59-163559) in which a predetermined range $\alpha°$ is set for the noise phase angle as shown in FIG. 10. Any indication in this range is regarded as a noise indication and is therefore masked so as to remove the effect of the noise. In this diagram, reference symbols p and q indicate a noise signal and a defect signal, respectively.

Figure 11:
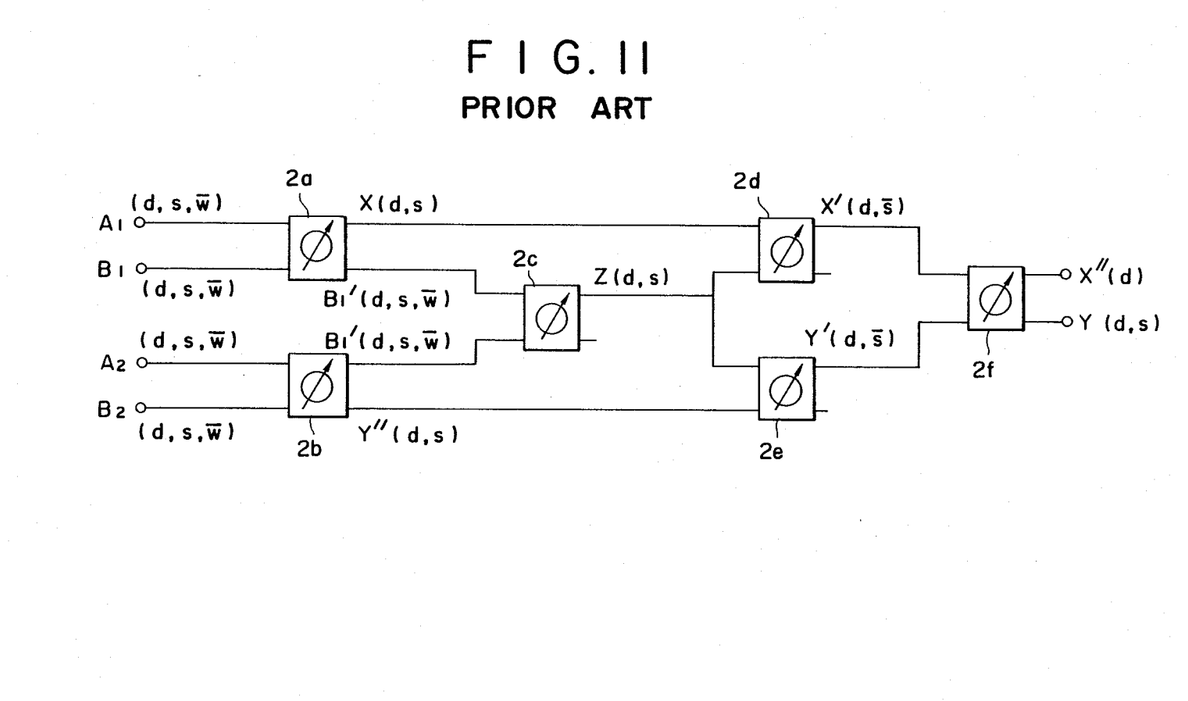

On the other hand, in a case including a plurality of noise factors, there has been conventionally used a method in which a plurality of (multiple) test frequencies are used corresponding to the noise factors. FIG. 11 shows an example of such a method in which reference numerals $2a$–$2f$ are coordinate rotating units. The rotation angles thereof are appropriately set beforehand so that the indication of each noise factor matches with the coordinate axis. In a multidimensional space finally comprising orthogonal axes of the phase detection outputs associated with the respective test frequency, a direction orthogonal to the indication of each noise factor is selected, thereby detecting a signal corresponding to the factor or parameter of the detection object to be measured without being effected from the noise ("Eddy Current Defecting Test B", NDI, '85, p. 118)., In FIG. 11, reference symbol d indicates a defect and reference symbols s and w denote noise factors.

In addition, the following method has also been disclosed as a simplified version of the method described above. In this method, two test frequencies are used. First, the vector plane is subjected to a coordinate rotation so that the component of the noise factor related with a first frequency of these frequencies and that related with a second frequency thereof match with one of the orthogonal axes of a vector plane of each frequency. Thereafter, a component orthogonal to the noise factor component related to the first frequency and a component orthogonal to the defect factor component related to the second frequency are extracted, and then these components are set to be orthogonal to each other in a new vector plane, thereby discriminating the defect factor and the noise factor based on the trace of signals on the plane (Japanese patent laid-open No. 60-146149).

As described above, in any conventional example described above, a phase angle or a phase angle range of the noise indication is beforehand examined and then the signal processing is accomplished by use of the coordinate rotation angle set according to the examined data.

However, the phase angle is actually subject to fluctuation because of variations in the lift-off, the coil temperature, the temperature of the test object, and electric characteristics (such as the electric conductivity and the magnetic permeability). Consequently, even if a phase angle or a phase angle range is beforehand established as in the case of the conventional example, the coordinate rotation angle is actually changed. Even if the coordinate rotation angle is slightly varied, the precision of the detection and measurement of the ECT is greatly deteriorated.

SUMMARY OF THE INVENTION

It is therefore and object of the present invention to provide a signal processing method in an electromagnetic induction test in which the onerous processing of examining beforehand the phase angle of each factor and setting the examined data to the pertinent coordinate rotating unit is not necessary and all factors effecting the ECT are simply discriminated with high precision regardless of the fluctuation in the detecting and measuring conditions, thereby solving the problems of the prior art ECT.

To achieve these objects, according to the present invention, in an electromagnetic induction test, a test object is subjected to an electromagnetic induction by the use of N (N≧1) kinds of test frequencies. M (M≦2N) kinds of phase detection outputs are obtained corresponding to the respective states of the test object, when there exist n(n<M) kinds of disturbance factors. A portion of these contribute to the ECT. The phase detection outputs have the variance in a fixed measurement interval greater than the variance of a portion of the factor of the detection/measurement object and contribute to the ECT in the fixed measurement interval. The phase detection outputs at a plurality of measuring points are sampled for each measurement interval. A first coordinate axis $Z_1$ is determined in a direction in which the variance of the distribution of the group of the measuring points comes to be a maximum in an M-dimensional space formed with the coordinate axes associated with the M kinds of the phase detection outputs. A second coordinate axis $Z_2$ is determined in a direction in which the variance of the distribution of the group of the measuring points comes to be a maximum in a space orthogonal to the coordinate axis $Z_1$ of the multidimensional space. Then a third coordinate axis $Z_3$, a fourth coordinate axis $Z_4$, ..., and an M-th coordinate axis $Z_M$ are similarly determined. Thereafter based on the coordinate of each said measuring point viewed from the coordinate axis $Z_{n+1}$, a measuring is effected to determine a presence or an absence of a defect, a physical quantity, and a geometric quantity on a surface of the test object or in the neighborhood thereof.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENT

Figure 1:
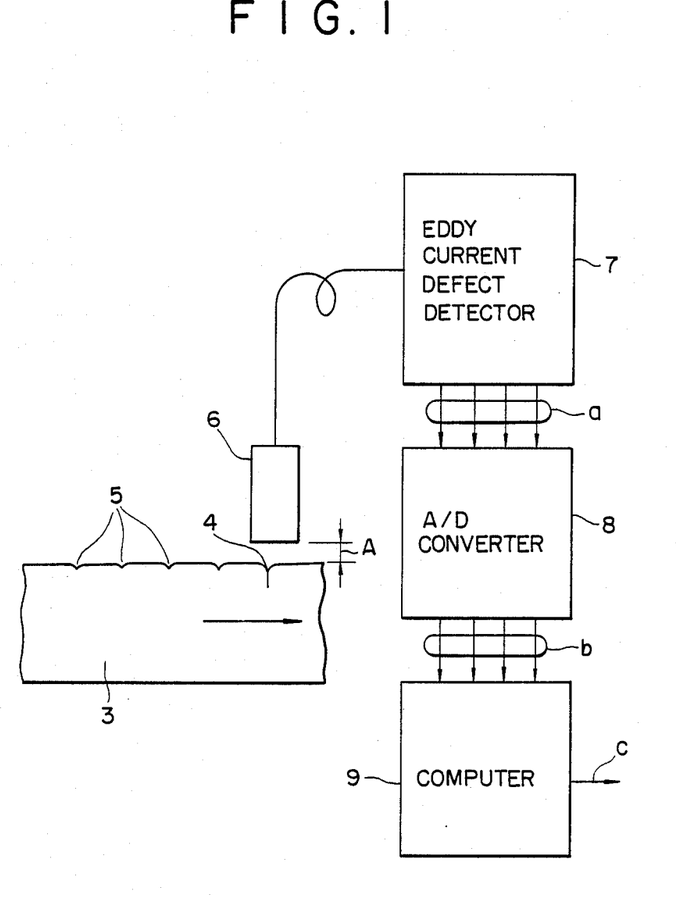
FIG. 1 is a block diagram of an apparatus to be used in an embodiment of the present invention.
Figure 2:
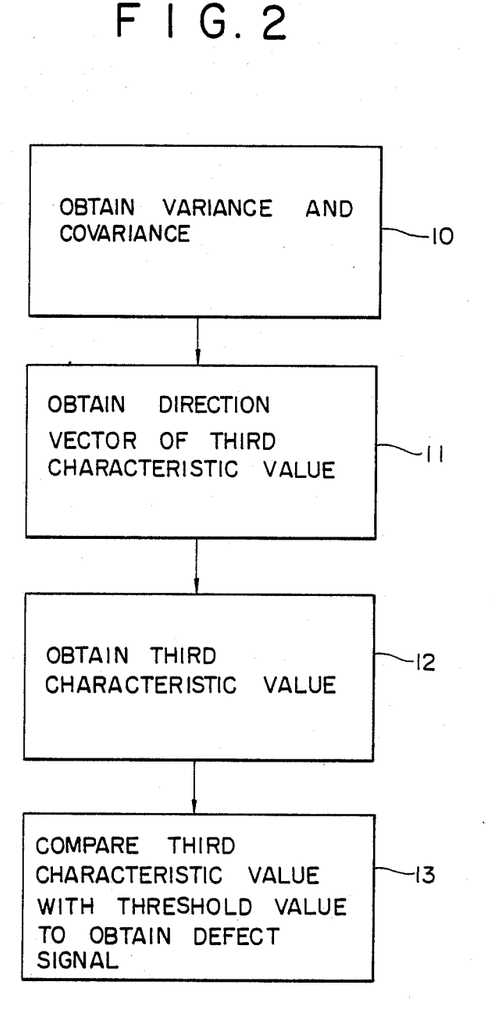
FIG. 2 is a flowchart illustrating a signal processing of the apparatus.
Figure 3A:
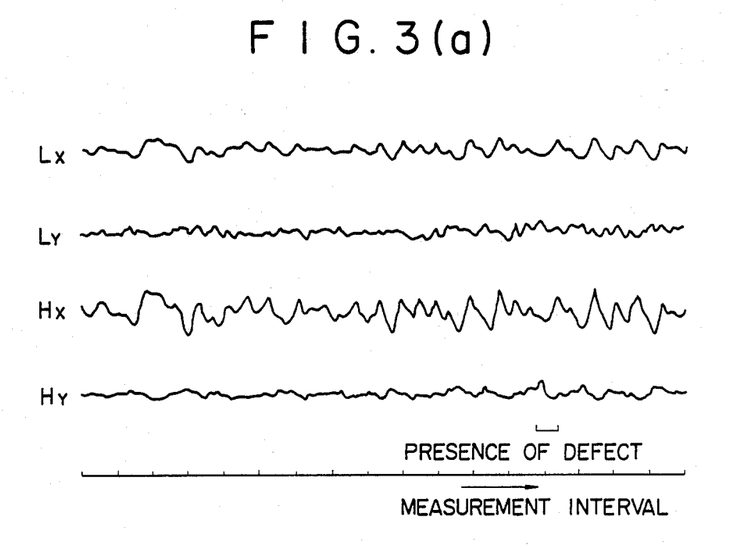
FIGS. 3a-3b are diagrams illustrating output waveforms of the signal processing of the embodiment.
Figure 3B:
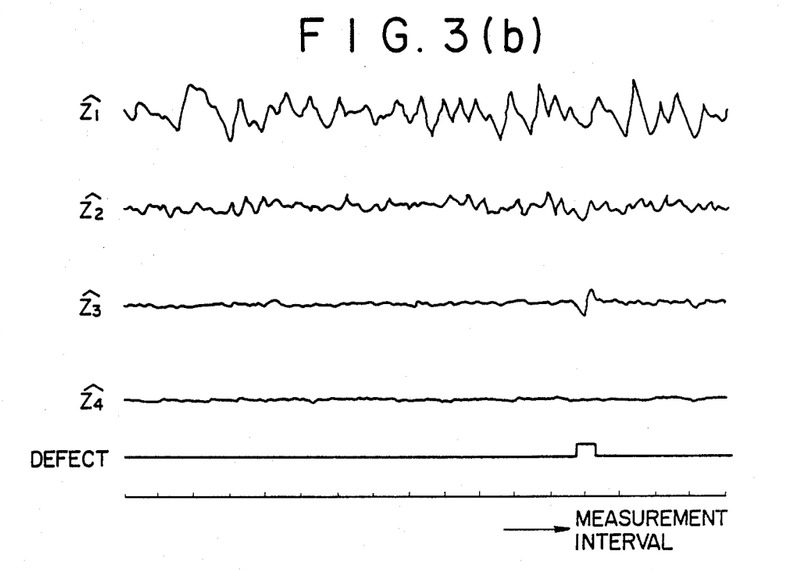

Various other objects, features and attendant advantages of the present invention wll be more fully appreciated as the same becomes better understood from the following detailed description when considered in connection with the accompanying drawings in which like reference characters designate like or corresponding parts throughout the several views and wherein:

FIG. 1 shows a block diagram of an apparatus to be used in an embodiment of a signal processing method according to the present invention, FIG. 2 is a flowchart of the signal processing of the apparatus, and FIGS. 3a-3b respectively illustrate signal output waveforms of the apparatus.

This embodiment illustrates a case of a hot defect detection where the ECT is used to detect a defect of a slab in a continuous casting for an as-cast while the slab is in the red-hot state.

As shown in FIG. 1, the continuously cast slab 3 being carried is provided with an oscillation mark 5 in addition to a surface defect 4 as a factor or parameter of the detection object to be measured. A probe 6 is located in the vicinity of the surface of the continuously cast slab 3, so that an alternating current having two kinds of frequencies (i.e. a high frequency and a low frequency) flowing through the coil (not shown) causes an eddy current to flow through the slab 3.

In this case, the noise factors include a variation of the lift-off A and the oscillation mark 5. The surface defect 4, the variation of the lift-off A, and the oscillation mark 5 are events independent to each other. Since the test object is a contnuously cast slab 3 for an as-cast, there exist a lot of undulations in the surface thereof, whereas few surface defects 4 occur, due to the recent improvement of the operation technique. Consequently, the defect detection is effected under a condition where the signal change is predominantly caused by the variation of the lift-off A and the oscillation mark 5 as compared with the surface defect 4 of the detection object.

As a stage subsequent to the probe 6, there is disposed a 2-frequency eddy current defect detector 7 which effects an amplification/phase detection on the defect signal from the probe 6 to obtain an analog phase detection signal a ($H_x$, $H_y$ on the high-frequency side; $L_x$ and $L_y$ on the low-frequency side). Reference numeral 8 indicates an A/D converter for converting the analog phase detection signal into a digital signal and outputs a digital phase detection output b, which is in turn processed by a computer 9 at the next stage, thereby obtaining a defect signal c corresponding to the factor or parameter of the detection object to be measured, namely, the surface defect. The signal processing of the computer 9 is conducted according to the flowchart of FIG. 2.

Next, a description will be given of a procedure of the signal processing method effected by use of the apparatus described above.

(2) While the slab 3 in the continuous casting is being transported, for each fixed interval along the casting (longitudinal) direction, a plurality of digital phase detection outputs b are sampled at a fixed interval through the probe 6, the 2-frequency eddy current defect detector 7, and the A/D converter 8. These are sequentially inputted in the computer 9 (not shown) at the next stage so as to be stored therein.

(2) The data obtained at a plurality of the measuring points, namely, the digital phase detection outputs b stored in the memory are supplied as a first step 10 of the program shown in FIG. 2, thereby obtaining the variance/covariance matrix with respect to the group of the measuring points.

That is, when the number i is assigned in the range from $i_o$ to $i_o+N-1$ to the N items of the digital phase detection outputs b sampled in the fixed interval of the continuously cast slab 3, the variance $S_{11}$ of Lx is obtained as:

$$S_{11} = \frac{\sum_{i=io}^{io+N-1} L_{xi}^2 - \frac{\left(\sum_{i=io}^{io+N-1} L_{xi}\right)^2}{N}}{N-1} \quad (1)$$

The variance $S_{22}$ of Ly, and variance $S_{33}$ of Hx and the variance $S_{44}$ of Hy are also obtained in the similar manner.

The covariance $S_{12}$ of Lx and Ly is obtained as:

$$S_{12} = \frac{\sum_{i=io}^{io+N-1} L_{xi}L_{yi} - \frac{\left(\sum_{i=io}^{io+N-1} L_{xi}\right)\left(\sum_{i=io}^{io+N-1} L_{yi}\right)}{N}}{N-1} \quad (2)$$

The covariances $S_{13}$, $S_{14}$, $S_{23}$, $S_{24}$ and $S_{34}$ of Lx and Hx, Lx and Hy, Ly and Hx, Ly and Hy and Hx and Hy, respectively are also attained in a similar fashion. From these results, the variance/covariance matrix is obtained as:

$$\begin{pmatrix} S_{11} & S_{12} & S_{13} & S_{14} \\ S_{12} & S_{22} & S_{23} & S_{24} \\ S_{13} & S_{23} & S_{33} & S_{34} \\ S_{14} & S_{24} & S_{34} & S_{44} \end{pmatrix} \quad (3)$$

(3) In a second step 11 of the logic processing in the computer 9, a direction vector of the third characteristic value based on the variance/covariance matrix is obtained. The direction vector of the third characteristic value is determined as follows. Namely, in a 4-dimensional space (Lx, Ly, Hx, Hy) formed with the coordinate axes associated with the respective digital phase detection outputs b, a direction in which the variance of the distribution of the group of the measuring points, namely, the N sampled digital phase detection ouputs b comes to be a maximum is defined to be a direction of the first characteristic value and a coordinate axis $Z_1$ is set in this direction. Next, a direction in which the variance of the distribution of the group of the measuring points comes to be a maximum in a 3-dimensional space orthogonal to the coordinate axis $Z_1$ in the 4-dimensional space is defined to be a direction of the second characteristic value and a coordinate axis $Z_2$ is set in this direction. And then a direction in which the variance of the distribution of the group of the measuring points comes to be a maximum in a 2-dimensional plane orthogonal to the coordinate axis $Z_2$ in the 3-dimensional space is defined as a direction of the third characteristic value and a unit vector in this direction is defined as a direction vector of the third characteristic value, and then a coordinate axis $Z_3$ is set along this direction. A direction orthogonal to the coordinate axis $Z_3$ is then uniquely determined in the 2-dimensional plane. In this direction, a coordinate axis $Z_4$ is set as a direction of the fourth characteristic value.

The sequence of the variances corresponds to the magnitude of the influence of each factor having an effect on the ECT, which is set as follows in this embodiment:

Variation of lift-off > Oscillation mark 5 > Surface defect 4.

Consequently, the third characteristic value comes to correspond to the surface defect 4 of the detection object.

Assuming here the eigenvalues of the variance/covariance matrix to be $\lambda_1$, $\lambda_2$, $\lambda_3$, and $\lambda_4$ in the descending order of the values, these eigenvalues correspond to the first, second, third, and fourth characteristic values, respectively. Consequently, an eigenvalue $\lambda_3$ is selected from these values as a variance of the third characteristic value corresponding to the surface defect of the detection object, and hence an eigenvector ($l_{31}$, $l_{32}$, $l_{33}$, $l_{34}$) is determined for the eigenvalue $\lambda_3$, namely, a direction vector of the third characteristic value is attained.

(4) Based on the direction vector extracted from the analysis on the primary component, a third step 12 of the logic processing sequentially reads the sampling data associated with the fixed measurement interval and stored in the memory, thereafter, the third characteristic value $Z_3$ is obtained as follows.

$$Z_3 = l_{31}L_x + l_{32}L_y + l_{33}H_x + l_{34}H_y \quad (4)$$

(5) The third characteristic value $Z_3$ thus obtained is compared with a predetermined threshold value in a third step 13 of the logic processing. If the third characteristic value $Z_3$ is greater than the predetermined threshold value, the third characteristic value $Z_3$ is assumed to be a defect signal c and is outputted from the computer 9.

While the logic processing is being carried out, the measured data obtained by sampling data in the next fixed interval of the continuously cast slab 3 is sequentially inputted through the probe 6, the 2-frequency eddy current defect detector 7, and the A/D converter 8 to the memory of the computer. The data is subjected to the logic processing during the next sampling interval in the similar manner as described above. In this fashion, a substantially realtime processing of the defect detection is continuously effected on the continuously cast slab 3 being transported.

FIGS. 3a–3b show respective output waveforms of the signal processing in this embodiment in which FIG. 3a illustrates the phase detection output and FIG. 3b depicts the characteristic value output. From these diagrams, it can be confirmed that the defect signal is clearly indicated in the third characteristic value $Z_3$. As compared with the value of S/N=1.2 (approx.) obtained when the defect is evaluated by use of Hy, the value of S/N=3.5 (approx.) results from this method, namely, the S/N value is greately improved and it has been confirmed that the measurement accuracy is considerably improved.

Although the embodiment has been described in a case where the detection is achieved only for the surface defect 4 of the continuously cast slab 3 as the test object, the similar manner is applicable, if necessary, to the detection of other factors, for example, the lift-off A and the oscillation mark 5 by obtaining the first characteristic value $Z_1$ and the second characteristic value $Z_2$.

Although the signal processing of this embodiment is accomplished through the analysis of the primary component in the 4-dimensional space by using two frequencies, so far as the following two requirements are satisfied;

① each factor effecting the ECT is an independent event and
② there exists a difference between the respective variances then, by effecting the primary component analysis in the multidimensional space by the use of at least two kinds of frequencies, this method is naturally applicable not only to the defect detection of a test object but also to the measurement of the physical and geometric quantities such as the electric conductivity, magnetic permeability, hardness, thickness, shape, and distance of the test object.

EMBODIMENT 2

Figure 4:
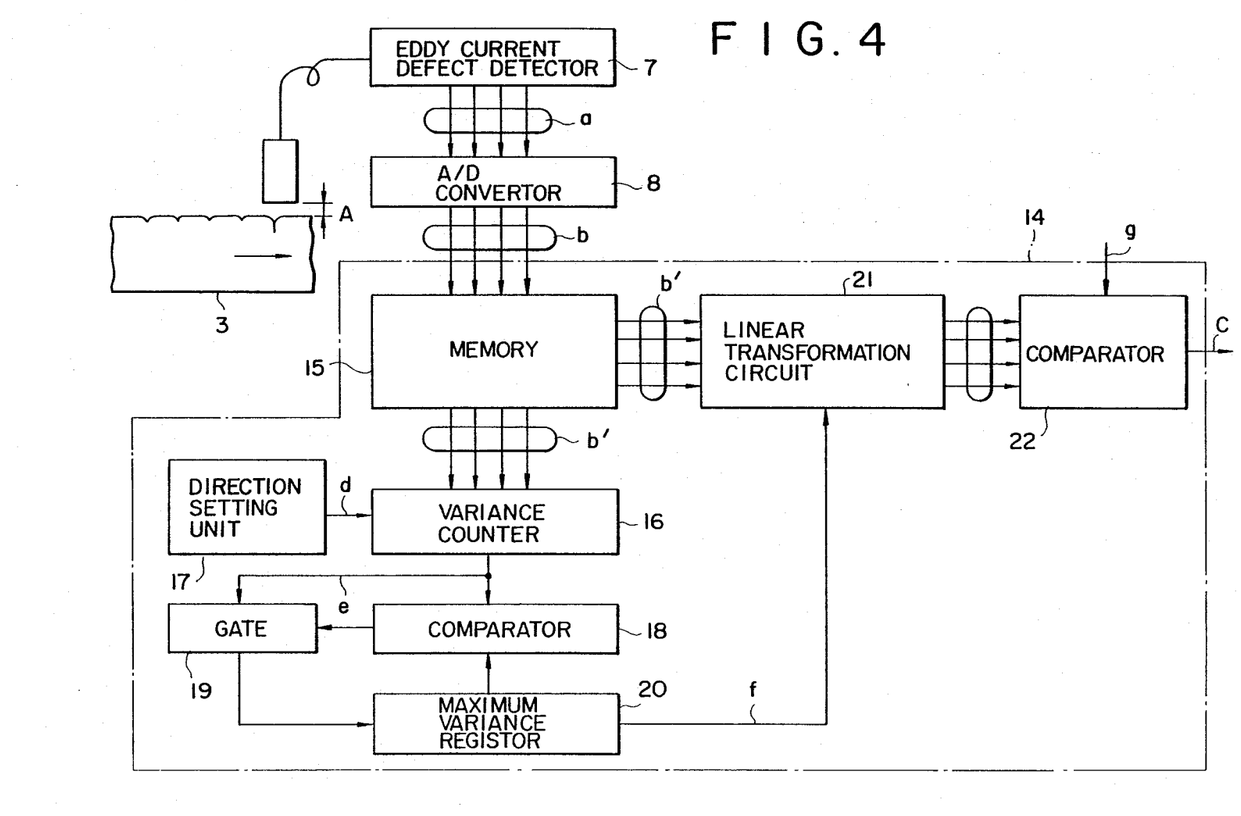
FIG. 4 is a block diagram of an apparatus to be used in another embodiment of the present invention.

FIG. 4 shows a block diagram of an apparatus to be used in another embodiment of the signal processing method according to the present invention.

The signal processing method of this embodiment will be described in conjunction with the apparatus. For the same components as those of the preceding embodiment, the same reference numerals are assigned thereto and the description thereof will be omitted.

(1) A plurality of measured data (digital phase detection outputs b') sampled for each fixed interval of the continuously cast slab 3 in the casting (longitudinal) direction and stored in a memory 15 of a computer 14 are inputted to a variance counter 16.

On the other hand, from a direction setting apparatus 17, a direction vector d ($l_1$, $l_2$, $l_3$, $l_4$) of the 4-dimensional space (Lx, Ly, Hx, Hy) formed with the coordinate axes of the respective phase detection outputs with respect to all directions is sequentially supplied to the variance counter 16. In the variance counter 16, the variance of the distribution configured by the group of the measurement points subjected to the sampling in the fixed interval is calculated for each direction vector d thus supplied thereto, and the attained output e is compared with a threshold value in a comparator 18. If the output e exceeds the threshold value, a gate 19 opens and the output e is sequentially transmitted to a maximum variance register 20. In the maximum variance register 40, each time a value exceeding a previously stored value is inputted thereto, the stored content is updated to be the greater value, and the content stored in the maximum variance register 20 is inputted to the comparator 18 as the threshold value for the next output from the variance counter 16. In this manner, a direction vector corresponding to the maximum value finally stored in the maximum variance register 20 is searched as the direction vector f ($\hat{l}_1$, $\hat{l}_2$, $\hat{l}_3$, $\hat{l}_4$) having the maximum variance.

Assuming here that a new coordinate axis Zn is set in a direction in the 4-dimensional space (Lx, Ly, Hx, Hy), the value on the coordinate axis Zn can be expressed by use of the direction vector d ($l_1$, $l_2$, $l_3$, $l_4$) as follows.

$$Zn = l_1 L_x + l_2 L_y + l_3 H_x + l_4 H_y \text{(where } l_1^2 + l_2^2 + l_3^2 + l_4^2 = 1) \quad (5)$$

If the number i ranging from $i_o$ to $i_o + N - 1$ is assigned to the data sampled at N measuring points, the variance S of the data in the predetermined measuring interval in the direction of the coordinate axis $Z_n$ can be represented as follows as already described in conjunction with the preceding embodiment.

$$S = \sum_{i=io}^{io+N-1} (Z_{ni} - \overline{Z}_n)^2 / (N - 1) \quad (6)$$

-continued $$\text{where } \overline{Z}_n = \sum_{i=io}^{io+N-1} Z_{ni}/N$$

Here, the direction vector having the maximum value of the variance S is ($\hat{l}_1$, $\hat{l}_2$, $\hat{l}_3$, $\hat{l}_4$).

(2) The direction vector f ($\hat{l}_1$, $\hat{l}_2$, $\hat{l}_3$, $\hat{l}_4$) of the maximum variance obtained as described above is then transmitted to a linear transformation unit 21, which sequentially reads the measurement data stored in the memory 15 to obtain the first characteristic value Z, as follows.

$$Z_1 = \hat{l}_1 L_x + \hat{l}_2 L_y + \hat{l}_3 H_x + \hat{l}_4 H_y \quad (7)$$

(3) After the first characteristic value Z, is attained, the direction setting apparatus 17 sequentially supplies the direction vector with respect to all directions in the 3-dimensional space orthogonal to the direction vector ($\hat{l}_1$, $\hat{l}_2$, $\hat{l}_3$, $\hat{l}_4$) of the first characteristic value Z, in the 4-dimensional space (Lx, Ly, Hx, Hy), thereby determining the second characteristic value $Z_2$ in the similar manner as for the preceding case. Similarly, the third and fourth characteristic values $Z_3$ and $Z_4$ are calculated by repeating the processing described above.

(4) As described in conjunction with the foregoing embodiment, the surface defect 4 of the test object corresponds to the third characteristic value $Z_3$, and hence the comparator 22 compares the threshold value g with the third characteristic value $Z_3$, and if the threshold value is exceeded, the third characteristic value $Z_3$ is outputted as a defect signal c from the computer 14.

Under the conditions of the measurement in this case, the first characteristic value $Z_1$ and the second characteristic value $Z_2$ correspond to the variation of the lift-off A and the oscillation mark 5, respectively as already described in conjunction with the preceding embodiment.

EMBODIMENT 3

Figure 5:
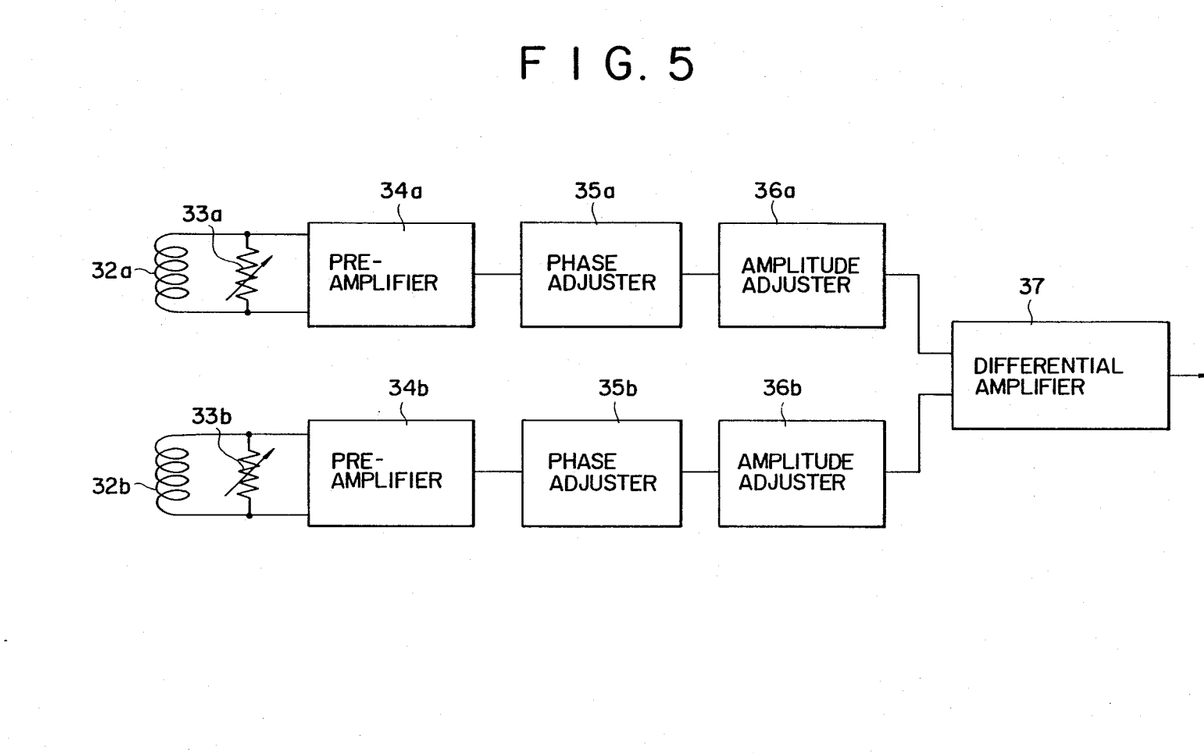
FIG. 5 is a block diagram showing a circuit configuration of an eddy current defect detector as an embodiment of the present invention.

FIG. 5 is a block diagram showing a circuit configuration of a portion ranging from the differential probe to the section obtaining the differential output in the eddy current defect detector as an embodiment of the present invention.

In this diagram, two detecting coils 32a and 32b are respectively connected to variable resistors 33a and 33b in parallel. When the resistance values of these variable resistors 33a and 33b are appropriately adjusted, the output change directions of the detecting coils 32a and 32b are rotated so as to match with each other. At the next stage of the detecting coils 32a and 32b, there are connected phase adjusters 35a and 35b via preamplifiers 34a and 34b, respectively. The phases of the outputs from the detecting coils 32a and 32b amplified by the preamplifiers 32a and 34b can be matched with each other by adjusting these phase adjusters 35a and 35b. In addition, as the next stage of the respective phase adjusters 35a and 35b, amplitude adjusters 36a and 36b are connected thereto, so that the amplitude values of the outputs from the detecting coils 32a and 32b are matched with each other by adjusting these amplitude adjusters 36a and 36b. The outputs from the respective amplitude adjusters 36a and 36b obtained when the output change directions, phases, and amplitudes are respectively matched with each other for a change of the lift-off are delivered to the inputs of the differential amplifier 37, thereby obtaining the difference between these two input signals. The differential output from the differential amplifier 37 is supplied to a signal processing section of the main section of the eddy current defect detector (not shown).

Figure 6:
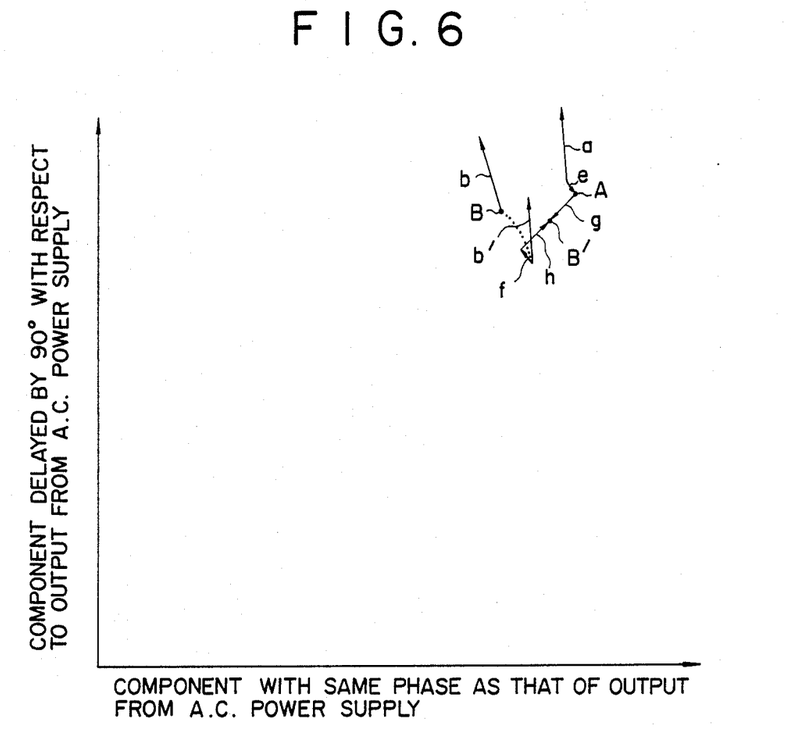
FIG. 6 is an explanatory diagram illustrating an output adjust procedure of the apparatus.

FIG. 6 shows a procedure to adjust the outputs from the detecting coils 32a and 32b of the defect detector.

In FIG. 6, for outputs A and B from the detecting coils 32a and 32b, respectively before the adjustment, the change directions of the outputs with respect to the variation of the lift-off are attended with a slight difference as shown by the arrow marks a and b. For example, when the variable resistance 33b on the side of the detecting coil 32b is adjusted to set the change direction of the output B for the lift-off change as indicated by an arrow mark b' and to match the resultant direction with the change direction a of the output A. With this adjustment, the output B is simultaneously changed to be B'. Next, by use of the phase adjusters 35a and 35b, the phases of the outputs A and B' are adjust to match with each other, which causes the outputs A and B' to change as indicated by arrow marks e and f in FIG. 6. Moreover, by use of the amplitude adjusters 36a and 36b, the amplitude values of the outputs A and B' are adjusted to match with each other, which causes the outputs A and B' as indicated by arrow marks g and h in FIG. 2.

Through repeating the adjusting operations several times, the outputs from two detecting coils 32a and 32b are adjusted to match with each other with respect to the phase and amplitude as well as to the output change direction for the lift-off change. In the example above, although the variable resistance 33b is adjusted, the other variable resistance 33a or both resistances may be adjusted.

Figures 7A, 7B:
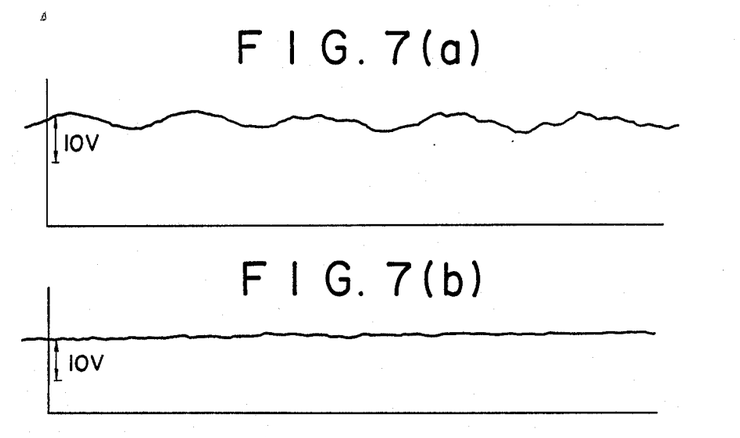
FIGS. 7a-7b are diagrams showing output waveforms of the apparatus of the embodiment.

FIG. 7 shows the experiment data (indicating the output component in the orthogonal direction of the display screen) obtained by the hot defect detection on a continuously cast slab by use of this system in which the waveform is compared with the output waveform of the conventional apparatus.

It can be seen from this diagram that as compared with the output waveform of the conventional apparatus shown in (a) of this figure in which the noise due to the lift-off change is included and hence the S/N value is deteriorated, the output waveform of the apparatus of the present invention shown in (b) does not include the noise due to the lift-off change and hence the S/N value is improved. Namely, in the comparative experiment, the S/N value of the detection output for a defect having a depth of 2 mm and a length of 20 mm is 0.6 in the conventional apparatus. The S/N value is improved to be 3.5 by the apparatus of the present invention.

Figure 8:
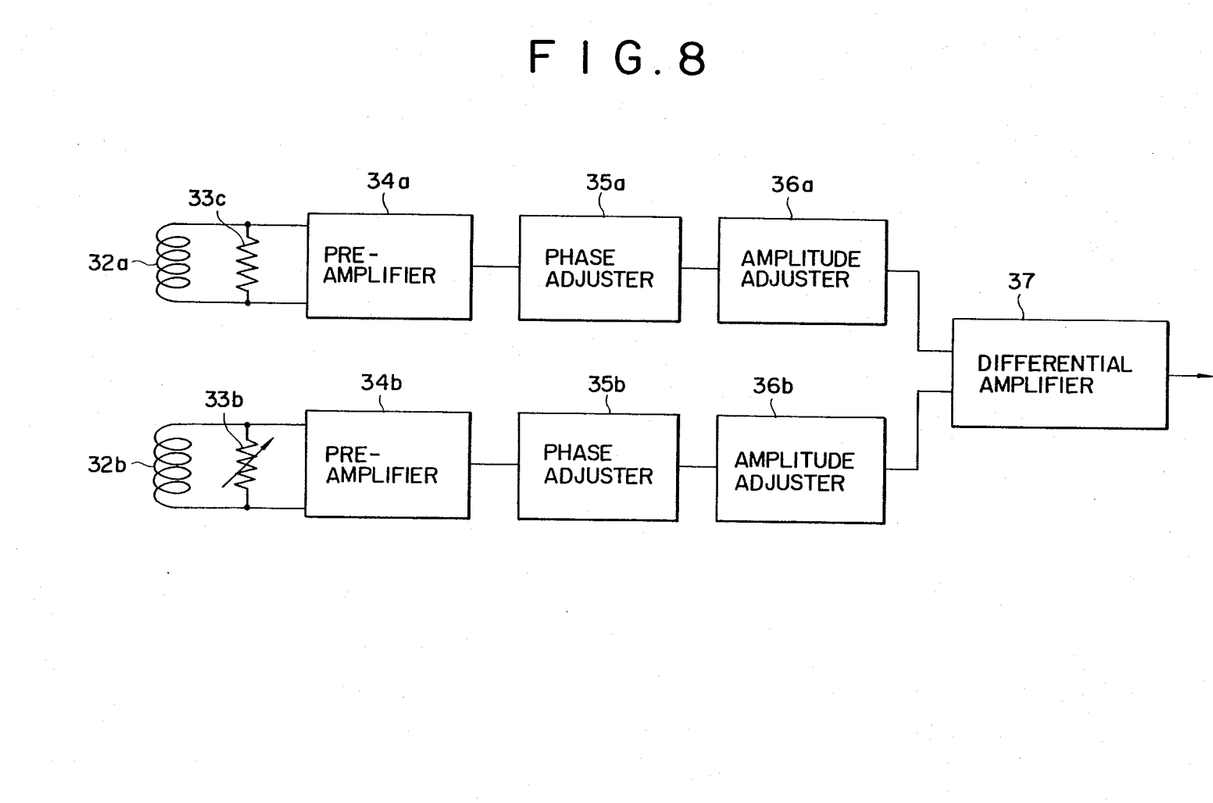
FIG. 8 is a block diagram illustrating a variation of the eddy current defect detector of the present invention.

As for the resistors to adjust the output change direction for the lift-off change, as shown in FIG. 8, the system may be configured such that a fixed resistor 33c is connected to the detection coil 32a and only a variable resistor 33b adjustable to a value in the neighborhood of the resistance value of the fixed registor 33c is connected to the detecting coil 32b. Although the embodiment includes a parallel connection of the resistor, the present invention is not restricted by such a parallel connection. Namely, any means that can appropriately adjust the direction of the output change corresponding to the lift-off change of the coil is applicable. Also in this case, the same effect as for the embodiment above can be implemented.

As described above, according to the signal processing of the present invention, the troublesome preparative processing required prior to an electromagnetic induction test in the conventional example to beforehand examine a phase angle of each factor and to set the obtained data to the coordinate rotating unit becomes unnecessary, which enables to effect the test in a considerably simple fashion.

In addition, since the phase angle corresponding to each factor can be necessarily determined by the restraint condition that the variance of the distribution formed with the measuring points to be sampled in a fixed measurement interval becomes to be maximum, the phase angle corresponding to each factor can be obtained so far as there exists a difference between the variances of the respective factors, which greatly improves the accuracy of the detection of the defect and the measurement of the physical and geometric quantities. Particularly, the phase angle can be attained by use of the measured data of the test object actually being subjected to the defect detection or the measurement and is consequently not apt to be influence by the change of the detecting or measuring condition, which further improves the accuracy of the measurement. Furthermore, all factors effecting the electromagnetic induction test can be discriminated, which leads to an effect, for example, a plurality of kinds of quantities are simultaneously measured.

Moreover, according to the eddy current defect detector of the present invention, not only the phases and amplitudes of the outputs from the two detection coils of the differential probe, but also the output direction changes with respect to the lift-off change can be matched with each other, and hence the noise caused by the lift-off change can be completely removed from the detection output, thereby leading to the effect that the S/N value is improved and also a very small defect is easily detected.

While the present invention has been described with reference to the particular illustrative embodiments, it is not to be restricted by those embodiments but by the appended claims. It is to be appreciated that those skilled in the art can change or modify the embodiments without departing from the scope and spirit of the present invention.

We claim:

1. A signal processing method in an electromagnetic induction test for detecting defects, physical quantities and geometric quantities in a surface of a test object in which said test object is subjected to an electromagnetic induction by use of $N(N \geq 1)$ kinds of test frequencies to obtain $M(M \leq 2N)$ kinds of phase detection outputs corresponding to respective states of the test object said method comprising the steps of:

sampling the phase detection outputs at a plurality of measuring points, so that when there exists $n(n < M)$ kinds of disturbance factors of which a portion contribute to the electromagnetic induction test, said phase detection outputs have a variance due to said defects, physical quantities and geometric quantities greater than a variance of a target parameter of the test object and contribute to the electromagnetic induction test;

determining a first coordinate axis $Z_1$ in a direction in which said variance of said phase detection outputs approaches a maximum in an M-dimensional space formed from coordinate axes associated with the M kinds of the phase detection outputs;

determining a second coordinate axis $Z_2$ in a direction in which said variance of said phase detection outputs approaches a maximum in a space orthogonal to the coordinate axis $Z_1$ of the multi-dimensional space;

similarly determining a third coordinate axis $Z_3$, a fourth coordinate axis $Z_4, \ldots$, and an M-th coordinate axis $Z_m$ in directions in which said variance of said phase detection outputs approaches a maximum in a space orthogonal to the previously named axis of the multi-dimensional space; and determining a presence or an absence of a defect, a physical quantity and a geometric quantity on a surface or in the vicinity of the test object related to the coordinate of the $Z_{n+1}$ axis for each measuring point.

2. A signal processing method according to claim 1 wherein said coordinate axes $Z_1$, $Z_2$, $Z_3$, $Z_4$, and so on are set such that a variance/covariance matrix is obtained, said matrix being configured with phase detection outputs corresponding to said measuring points sampled, and said coordinate axes $Z_1$, $Z_2$, $Z_3$, $Z_4$, and so on are set so as to correspond to eigenvectors associated with eigenvalues $\lambda_1$, $\lambda_2$, $\lambda_3$, $\lambda_4$ of the variance/covariance matrix.

3. A signal processing method according to claim 1 wherein said coordinate axes $Z_1$, $Z_2$, $Z_3$, $Z_4$, and so on are set such that a variance of a distribution of the measuring points is sequentially obtained in all directions of said multidimensional space and a coordinate axis is set in a direction in which the variance becomes to be maximum.

4. A signal processing method according to claim 1, 2, or 3 wherein a defect is detected on a surface or in the neighborhood of a surface of a steel piece produced through a continuous casting by use of two kinds of frequencies including a low frequency and a high frequency.

5. A signal processing method according to claim 1, 2, or 3 wherein a defect is detected on a surface or in the neighborhood of a surface of a steel piece produced through a continuous casting by use of a kind of frequency.

* * * * *

UNITED STATES PATENT AND TRADEMARK OFFICE
CERTIFICATE OF CORRECTION

PATENT NO. : 4,823,082

DATED : April 18, 1989

INVENTOR(S) : Shoji Nasu, et al.

It is certified that error appears in the above-identified patent and that said Letters Patent is hereby corrected as shown below:

On the title page, the number of drawings is incorrect, it should read as follows:

--9--

Signed and Sealed this

Twentieth Day of October, 1992

Attest:

DOUGLAS B. COMER

*Attesting Officer*      *Acting Commissioner of Patents and Trademarks*